United States Patent
Yamaguchi et al.

(10) Patent No.: US 8,680,250 B2
(45) Date of Patent: Mar. 25, 2014

(54) METHOD AND DEVICE FOR EXTRACTING POLLEN PROTEINS

(75) Inventors: Tsuneo Yamaguchi, Otsuki (JP); Akira Saito, Toride (JP); Akio Kato, Yamaguchi (JP)

(73) Assignees: Wako Filter Technology Co., Ltd., Tokyo (JP); Protec Co., Ltd., Yamaguchi (JP)

( * ) Notice: Subject to any disclaimer, the term of this patent is extended or adjusted under 35 U.S.C. 154(b) by 0 days.

(21) Appl. No.: 13/320,738

(22) PCT Filed: May 10, 2010

(86) PCT No.: PCT/JP2010/057850
§ 371 (c)(1),
(2), (4) Date: Nov. 15, 2011

(87) PCT Pub. No.: WO2010/131611
PCT Pub. Date: Nov. 18, 2010

(65) Prior Publication Data
US 2012/0065382 A1    Mar. 15, 2012

(30) Foreign Application Priority Data
May 15, 2009   (JP) .................. 2009-118399

(51) Int. Cl.
*A23J 1/00* (2006.01)
*C07K 1/00* (2006.01)
*C07K 14/00* (2006.01)
*C07K 16/00* (2006.01)
*C07K 17/00* (2006.01)

(52) U.S. Cl.
USPC ....................................................... 530/412

(58) Field of Classification Search
None
See application file for complete search history.

(56) References Cited

U.S. PATENT DOCUMENTS

2007/0183978 A1* 8/2007 Preuss et al. ................. 424/9.81

FOREIGN PATENT DOCUMENTS

| CN | 1709141 A | 12/2005 |
|---|---|---|
| JP | 04099416 A | 3/1992 |
| JP | 07-188291 A | 7/1995 |
| JP | 07179494 A | 7/1995 |
| JP | 07-304794 A | 11/1995 |
| JP | 2001151797 A | 6/2001 |
| JP | 2004249179 A | 9/2004 |
| JP | 2005008576 A | 1/2005 |
| JP | 2006-340658 A | 12/2006 |
| JP | 2008141993 A | 6/2008 |
| SU | 952259 A1 | 8/1982 |

OTHER PUBLICATIONS

Kuldeep S. et al., "Isolation and identification of pollen allergens of *Artemisia scoparia*," journal of J. Allergy Clin. Immunol, Oct. 1987, 80(4), 562-572 pages.
Garcia-Ortega P. et al., "*Mercurialis annua*pollen: A new source of allergic sensitization and respiratory disease," Journal of J. Allergy Clin. Immunol., 1992, 89(5), 987-993 pages.
Russian Industrial Property Office, Office Action of Russian Patent Application No. 2011151088, Dec. 12, 2013, 9 pages.

* cited by examiner

*Primary Examiner* — Nora Rooney
(74) *Attorney, Agent, or Firm* — Alleman Hall McCoy Russell & Tuttle LLP

(57) ABSTRACT

The present invention is one that, in a pollen protein extracting method, enables mass production, and while improving production efficiency, achieves a reduction in workload such as a reduction in man-hours, reductions in equipment cost and running cost, and an improvement of a work environment. Specifically, a pollen protein extracting method for extracting water-soluble protein from pollen is characterized by including: mixing the pollen and PBS; adding an aggregating agent including a natural inorganic component to a resultant mixed solution and performing stirring; and after formation of a pollen aggregate, performing filter filtration to perform solid-liquid separation.

2 Claims, 2 Drawing Sheets

| | PRODUCT NAME | MAIN CONSTITUENT | IONICITY | USE CONCENTRATION | EVALUATION RESULT |
|---|---|---|---|---|---|
| NATURAL INORGANIC AGGREGATING AGENT | ZEOFLOC 30 | NATURAL MINERAL BASIS | NO | 0.001-0.03% | GOOD SEPARATION AFTER 30-MINUTES SETTLING |
| | ZEOFLOC 70 | NATURAL MINERAL BASIS | NO | 0.001-0.03% | GOOD SEPARATION AFTER 30-MINUTES SETTLING |
| | ZEOFLOC 70GWP | NATURAL MINERAL BASIS | NO | 0.001-0.03% | COMPLETE SEPARATION AFTER 30-MINUTES SETTLING, TRANSPARENT FILTRATE |
| | MI-1 (FOR LOW CONCENTRATION) | NATURAL INORGANIC MATERIAL | NO | 0.001-0.03% | GOOD SEPARATION AFTER 30-MINUTES SETTLING |
| | ZA-1 (FOR HIGH CONCENTRATION) | NATURAL INORGANIC MATERIAL | NO | 0.001-0.03% | GOOD SEPARATION AFTER 30-MINUTES SETTLING |
| POLYMER AGGREGATING AGENT | N-100 | POLYACRYLAMIDE | NONION | 0.05-0.2% | CANNOT ACHIEVE COMPLETE SEPARATION, LIQUID VISCOSITY UP, CANNNOT USE |
| | A-95H | POLYACRYLAMIDE | WEAK ANION | 0.05-0.2% | CANNOT ACHIEVE COMPLETE SEPARATION, LIQUID VISCOSITY UP, CANNNOT USE |
| | A-110L | POLYACRYLAMIDE | MEDIUM ANION | 0.05-0.2% | CANNOT ACHIEVE COMPLETE SEPARATION, LIQUID VISCOSITY UP, CANNNOT USE |
| | A-115 | POLYACRYLAMIDE | MEDIUM ANION | 0.05-0.2% | CANNOT ACHIEVE COMPLETE SEPARATION, LIQUID VISCOSITY UP, CANNNOT USE |
| | A-130H | POLYACRYLAMIDE | MEDIUM ANION | 0.05-0.2% | CANNOT ACHIEVE COMPLETE SEPARATION, LIQUID VISCOSITY UP, CANNNOT USE |
| | A-190 | SODIUM POLYACRYLATE | STRONG ANION | 0.05-0.2% | CANNOT ACHIEVE COMPLETE SEPARATION, LIQUID VISCOSITY UP, CANNNOT USE |
| | A-210 | MODIFIED POLYACRYLAMIDE SERIES | NONION | 0.05-0.2% | CANNOT ACHIEVE COMPLETE SEPARATION, LIQUID VISCOSITY UP, CANNNOT USE |
| | A-240 | MODIFIED POLYACRYLAMIDE SERIES | MEDIUM ANION | 0.05-0.2% | CANNOT ACHIEVE COMPLETE SEPARATION, LIQUID VISCOSITY UP, CANNNOT USE |

FIG.2

METHOD AND DEVICE FOR EXTRACTING POLLEN PROTEINS

TECHNICAL FIELD

The present invention relates to a pollen protein extracting method for extracting water-soluble protein from pollen, and an extracting device that is preferably used for the extracting method.

BACKGROUND ART

In recent years, as a food composition that suppresses an allergic reaction (hay fever) caused by cedar pollen, as disclosed in Patent literature 1, a food composition that includes cedar pollen allergen protein coated with an antigen structure by polysaccharide modification as an active ingredient and has an allergy suppressing effect based on oral immunologic tolerance is considered.

Also, as a method for extracting pollen allergen protein from cedar pollen, a method that mixes cedar pollen with a buffer solution to dissolve water-soluble protein in water from the cedar pollen, and then centrifuges the solution to thereby separate liquid containing the water-soluble protein and solid matter from each other is considered as disclosed in Patent literature 2.

However, the water-soluble protein extracting method using a centrifuge as described above has a limitation in a throughput per lot, and is therefore not suitable for large volume extraction. Also, workloads inherent in rotor attachment/detachment work before/after the centrifugation, cleaning work after the centrifugation, and the like are extremely large, and running cost is also increased.

Further, in order to perform large volume extraction and improve extraction efficiency, it is considered to prepare a large volume centrifuge, or a plurality of centrifuges; however, this increases not only equipment cost but also running cost, and is therefore not a good idea.

In addition, the method using a centrifuge has a problem that a work environment is deteriorated due to vibration, noise, and the like caused by the centrifuge.

Citation List

Patent Literature

[Patent literature 1] JPA 2006-340658
[Patent literature 2] JPA 1995-304794

SUMMARY OF INVENTION

Technical Problem

Therefore, the present invention is made to solve the above problems at once, and has a main desired object to, in extraction of cedar pollen allergen protein (hereinafter referred to as cedar pollen protein), make it possible to perform large volume extraction, and while improving extraction efficiency, reduce a workload, reduce equipment cost and running cost, and achieve an improvement of a work environment.

Solution to Problem

Accordingly, a pollen protein extracting method according to the present invention is a pollen protein extracting method for extracting water-soluble protein from pollen, and includes: mixing the pollen and phosphate buffered saline (hereinafter referred to as "PBS"); adding a natural inorganic aggregating agent to a resultant mixed solution and performing stirring; and after formation of a pollen aggregate, performing filter filtration to perform solid-liquid separation.

If so, on the basis of a filter filtration method, large-volume extraction can be performed to improve extraction efficiency. Also, what should be done is only to mix and stir the pollen, PBS, and natural inorganic aggregating agent and perform the filter filtration, and therefore the problems (workload, cost, work environment, and the like) in the conventional method using a centrifuge can be solved. Further, the aggregating agent is used to form the pollen aggregate, and then the solid-liquid separation is performed, so that even in the case of pollen having a particle size of 0.5 $\mu$m, a bridge phenomenon can be prevented early from appearing to clog a filter, and without losing a filter function, the separation can be surely performed. Still further, the natural inorganic aggregating agent is used to perform the extraction, and therefore the resultant pollen protein can be preferably used as an active ingredient of a food composition.

Also, the pollen is a difficult to collect raw material, and therefore preferably effectively utilized, and in addition to this, the water-soluble protein included in the pollen cannot be completely extracted only by the previous method. From such a point of view, preferably, the method further includes: crushing a cake formed on a filter by the filter filtration into powder, and then mixing the powder with phosphate buffered saline again; adding a natural inorganic aggregating agent and performing stirring; and after re-formation of a cedar pollen aggregate, performing filter filtration to perform solid-liquid separation.

Further, a pollen protein extracting device that is prefeably used for the above pollen protein extracting method is provided with: a mixing and stirring part that is configured to mix and stir pollen, PBS, and a natural inorganic aggregating agent; and a filter part that is configured to filtrate a mixed solution obtained by the mixing and stirring part to perform solid-liquid separation.

A method of the present invention is not limited to the method for extracting protein from cedar pollen, but can also be applied to a method for extracting protein from another plant pollen (for example, tree pollen such as alder pollen, white birch pollen, or cypress pollen, or pollen such as grass pollen or compositae pollen). In this case, a pollen protein extracting method of the present invention is a pollen protein extracting method for extracting water-soluble protein from pollen, and includes: mixing the pollen and a buffer solution; adding a natural inorganic aggregating agent to a resultant mixed solution and performing stirring; and after formation of a pollen aggregate, performing filter filtration to perform solid-liquid separation.

Advantageous Effects of Invention

According to the present invention configured as described, in extraction of cedar pollen proteins, it is possible to perform large volume extraction, and while improving extraction efficiency, reduce a workload, reduce equipment cost and running cost, and achieve an improvement of a work environment.

BRIEF DESCRIPTION OF THE DRAWINGS

FIG. 2 is a table illustrating comparison results between natural inorganic aggregating agents and polymer aggregating agents.

REFERENCE CHARACTERS LIST

Figure 1:
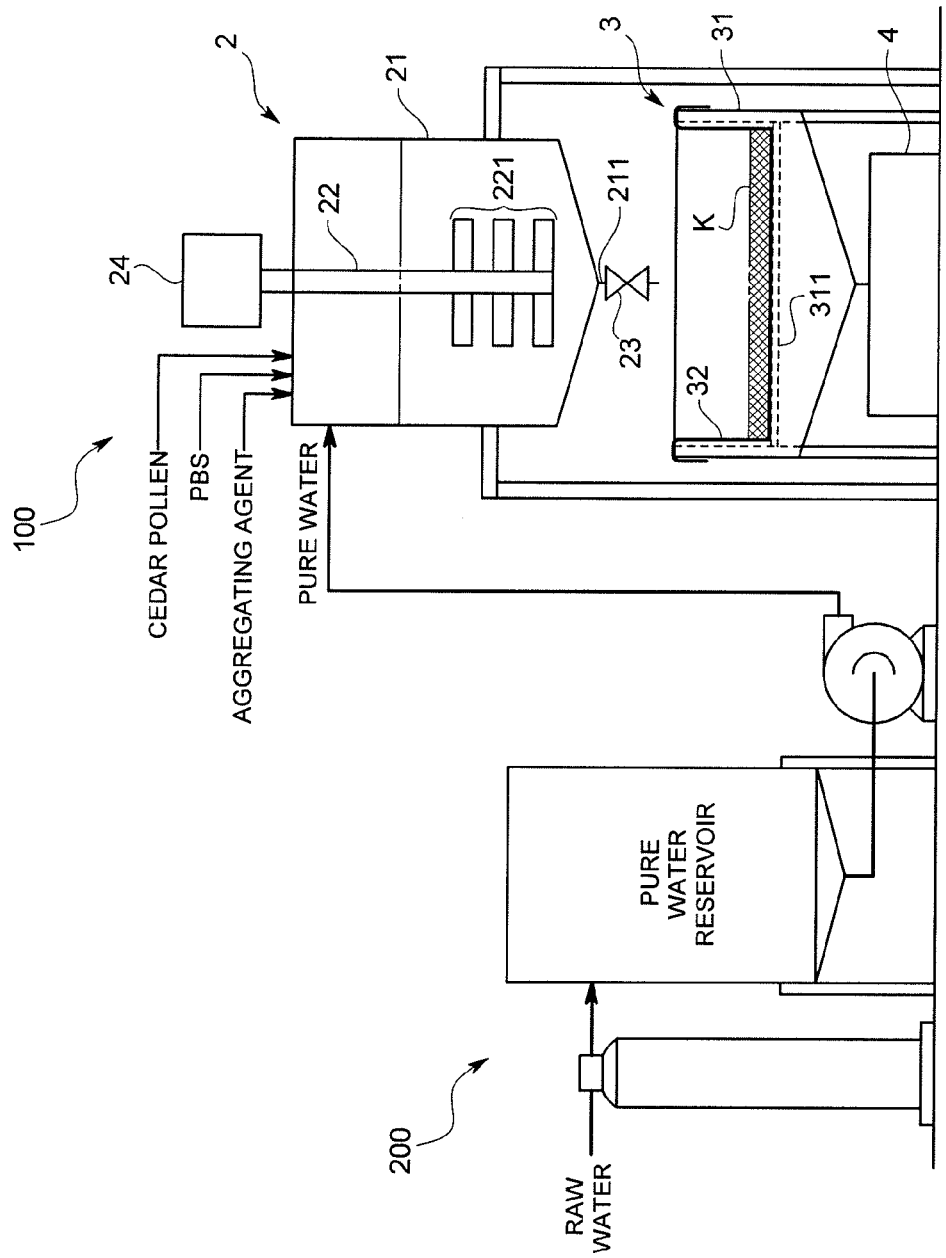
FIG. 1 is a schematic diagram illustrating a configuration of a cedar pollen protein extracting device according to one embodiment of the present invention.

100: Cedar pollen protein extracting device
2: Mixing and stirring part
21: Stirring tank
22: Stirring body
3: Filter part
4: Storage container
31: Filtration tank
32: Filtration filter

DESCRIPTION OF THE EMBODIMENTS

In the following, one embodiment of a cedar pollen protein extracting device according to the present invention is described referring to the drawings.

A cedar pollen protein extracting device 100 according to the present embodiment is one that extracts water-soluble protein included in cedar pollen by mixing the cedar pollen and PBS with each other to thereby dissolve the water-soluble protein in the PBS.

Specifically, this device is, as illustrated in FIG. 1, provided with: a mixing and stirring part 2; and a filter part 3 that is provided on a lower side of the mixing and stirring part and contains a detachable filtration filter 32 that filtrates a mixed solution obtained by the mixing and stirring part 2.

The mixing and stirring part 2 is provided with: a stirring tank 21 that contains cedar pollen, PBS, and aggregating agent; and a stirring body 22 that is provided in the stirring tank 21 and has stirring blades 221 that mixes and stirs the cedar pollen, PBS, and aggregating agent contained in the tank 21. The aggregating agent is one that aggregates the cedar pollen mixed in the PBS to form an aggregate (floc). Also, the PBS controls pH to thereby increase a protein extraction efficiency, and also fulfill a function of preventing the water-soluble protein of the cedar pollen from denaturing to enhance stability of the protein. In addition, Reference numeral 24 in FIG. 1 represents an actuator that drives the stirring body 22, such as a motor.

The stirring tank 21 is, in its upper part, provided with: a cedar pollen charging part for charging the cedar pollen; a PBS charging part for charging the PBS; and an aggregating agent charging part into which the natural inorganic aggregating agent is charged. Also, at the bottom of the mixing and stirring tank 21, a discharge port 211 for discharging outward the mixed solution formed by the mixing and stirring is formed, and the discharge port 211 is provided with an on-off valve 23.

Also, the stirring tank 21 is connected with a pure water production system 200, and supplied with pure water produced by the pure water production system 200 from an upper part of the stirring tank 21. On the basis of this, the stirring tank 21 is configured to adjust the PBS.

The filter part 3 is provided on a lower side of the discharge port 211 of the stirring tank 21, and provided with: a filtration tank 31 that is opened upward; and a filtration filter 32 that is arranged on a partition part 311 that is provided in the middle part of the filtration tank 31. The partition part 311 is formed with a plurality of through-holes that cause liquid having passed through the filtration filter 32 to flow downward. In the filter filtration of the mixed solution, a cake K including the aggregate of the cedar pollen is formed on the filtration filter 32, and also the liquid containing the cedar pollen protein passes to be thereby subjected to solid-liquid separation. Note that a thickness of the cake formed on the filtration filter 32 is controlled to at most 15 mm, and a size (area) of the filtration filter 32 is set depending on an amount of the mixed solution to be filtrated.

Also, the aggregating agent of the present embodiment is a powder aggregating agent including a natural inorganic component. In the following, the natural inorganic aggregating agent is described along with comparative examples of the cases of using polymer aggregating agents.

As the natural inorganic aggregating agent of the present embodiment, ZEOfloc 30, ZEOfloc 70, or ZEOfloc 70GWP manufactured by Kankyo Souken Co, Ltd., which contains calcium sulfate ($CaSO_4$), aluminum oxide ($Al_2O_3$), silicon dioxide ($SiO_2$), and aluminum sulfate ($Al_2SO_4$) as main constituents, or MI-1 (for low concentration) or ZA-1 (for high concentration) manufactured by SAN-IN PROSHEART CORP., which contains calcium, silicon, and the like as main constituents, is used. Note that if as the natural inorganic aggregating agent, an aggregating agent containing, as a main constituent, calcium silicate that is approved for use as a food additive is used, safety as a food product can be ensured.

On the other hand, as the polymer aggregating agent used for comparison, Accofloc (N-100 or the like) manufactured by MT AquaPolymer,Inc., which contains polyacrylamide, sodium polyacrylate, or modified polyacrylamide series as a main constituent is used.

Test and evaluation results of these natural inorganic aggregating agents and polymer aggregating agents are illustrated in FIG. 2. As can be seen from FIG. 2, it turns out that in the case of using any of the polymer aggregating agents to extract the cedar pollen protein, fluid viscosity is increased at the time of adding the aggregating agent, so that not only handling becomes difficult, but also solid matter such as the cedar pollen and the liquid cannot be completely separated from each other.

On the other hand, in the case of using any of the natural inorganic aggregating agents to extract the cedar pollen protein, it turns out that viscosity is not increased even when the natural inorganic aggregating agent is added, and as a result of filter filtration after 30-minute settling, a separation state is good as compared with the case of using any of the polymer aggregating agents. In particular, in the case of using Zeofloc 70GWP, it turns out that as a result of the filter filtration after 30-minute settling, transparent filtrate can be obtained, and the solid-liquid separation can be almost completely achieved.

Next, a cedar pollen protein extracting method using the cedar pollen protein extracting device 100 configured as described is described.

First, cedar pollen, pure water, and PBS are charged into the stirring tank 21 to mix the pollen in the PBS with the stirring body 22. Then, the natural inorganic aggregating agent is added and stirred with the stirring body 22. This causes the water-soluble protein in the cedar pollen to be dissolved in the PBS, and also a cedar pollen aggregate (floc) to be formed.

After the stirring has been completed, the on-off valve 23 of the discharge port 211 of the stirring tank 21 is opened to introduce the mixed solution into the filter part 3. Note that before the on-off valve 23 is opened, the filtration filter 32 is set in the filter part 3.

The mixed solution introduced into the filter part 3 flows onto the filtration filter 32; on the filtration filter 32, the cake including the cedar pollen aggregate is formed; and also, liquid containing the water-soluble protein in the cedar pollen, which has passed through the cake and the filtration filter 32, is accumulated in a storage container 4 provided below the filter part 3.

After the filter filtration has been completed, the cake formed on the filtration filter 32 is crushed into powder. Then, cedar pollen obtained by crushing the cake into the powder is again charged into the stirring tank 21 and mixed with the PBS. Then, the natural inorganic aggregating agent is added and stirred to again form a cedar pollen aggregate, and then filter filtration is performed to perform solid-liquid separation. As described, by crushing the cake and again performing the filtering filtration, the water-soluble proteins that are not extracted from the cedar pollen in the first attempt can be more completely extracted, and thereby the cedar pollen that is a raw material can be effectively utilized.

Effects of the Present Embodiment

According to the cedar pollen protein extracting method according to the present embodiment configured as described, on the basis of the filter filtration method, the extraction can be performed on a large scale as large as the case of using a centrifuge, which makes it possible to perform large-volume extraction of the cedar pollen protein to improve extraction efficiency. Also, what should be done is only to mix and stir the cedar pollen, PBS, and natural inorganic aggregating agent, and perform the filter filtration, and therefore the problems (workload, cost, work environment, and the like) in the conventional method using a centrifuge can be solved. Further, the aggregating agent is used to form the cedar pollen aggregate, and then the solid-liquid separation is performed, so that without losing a filter performance, the separation can be surely performed. Still further, the natural inorganic aggregating agent is used to perform the extraction, and therefore the resultant cedar pollen protein can be preferably used as an active ingredient of a food composition.

<Other Variations>

Note that the present invention is not limited to the above-described embodiment.

For example, the above-described embodiment is adapted to mix the cedar pollen and PBS with each other, and then add and stir the natural inorganic aggregating agent; however, the present invention may be adapted to simultaneously mix and stir the cedar pollen, PBS, and natural inorganic aggregating agent.

Also, the cedar pollen protein extraction in the above-described embodiment is performed in such a way that the cake formed on the filtration filter is crushed to again extract the cedar pollen protein; however, the present invention may be adapted to perform this multiple times.

Further, a buffer solution in the above-described embodiment is one using the PBS; however, in addition, even in the case of using a buffer solution that contains sodium hydrogen carbonate and sodium chloride, the same effects can be obtained.

In addition, in the above-described embodiment, the cedar pollen protein extracting method is described; however, the present invention can also be applied for a method for extracting protein from another plant pollen, for example, tree pollen such as alder pollen, white birch pollen, or cypress pollen, or pollen such as grass pollen or compositae pollen. In addition, base powder of PBS also may be used instead of PBS.

In addition, it should be appreciated that part or all of the above-described embodiment and variations may be appropriately combined, and the present invention is not limited to any of the above-described embodiments but can be variously modified without departing from the scope thereof.

INDUSTRIAL APPLICABILITY

Thus, according to the present invention, in extraction of cedar pollen protein, it is possible to perform large volume extraction, and while improving extraction efficiency, reduce a workload, reduce equipment cost and running cost, and achieve an improvement of a work environment.

The invention claimed is:

1. A pollen protein extracting method for extracting water-soluble protein from pollen, the method comprising:
   mixing the pollen and phosphate buffered saline;
   adding a natural inorganic aggregating agent consisting primarily of calcium silicate to a resultant mixed solution and performing stirring; and
   after formation of a pollen aggregate, performing filter filtration to perform solid-liquid separation to separate liquid containing water-soluble protein from the mixed solution.

2. The pollen protein extracting method according to claim 1, comprising:
   crushing a cake formed on a filter by the filter filtration into powder, and then mixing the powder with phosphate buffered saline again;
   adding the natural inorganic aggregating agent and performing stirring: and
   after re-formation of a pollen aggregate, performing filter filtration to perform solid-liquid separation.

* * * * *